United States Patent
Busch et al.

(10) Patent No.: US 8,588,367 B2
(45) Date of Patent: Nov. 19, 2013

(54) MOTION COMPENSATION IN QUANTITATIVE DATA ANALYSIS AND THERAPY

(75) Inventors: Marc Busch, Cologne (DE); Ralph Brinks, Hagen (DE)

(73) Assignee: Koninklijke Philips N.V., Eindhoven (NL)

( * ) Notice: Subject to any disclaimer, the term of this patent is extended or adjusted under 35 U.S.C. 154(b) by 629 days.

(21) Appl. No.: 12/525,080

(22) PCT Filed: Oct. 16, 2007

(86) PCT No.: PCT/US2007/081456
§ 371 (c)(1),
(2), (4) Date: Jun. 17, 2010

(87) PCT Pub. No.: WO2008/127368
PCT Pub. Date: Oct. 23, 2008

(65) Prior Publication Data
US 2010/0266099 A1    Oct. 21, 2010

Related U.S. Application Data

(60) Provisional application No. 60/888,561, filed on Feb. 7, 2007.

(51) Int. Cl.
*A61N 5/10* (2006.01)
*G01T 1/161* (2006.01)
*G01T 1/163* (2006.01)
*G01T 1/166* (2006.01)

(52) U.S. Cl.
USPC .............. 378/65; 250/363.02; 250/363.03; 250/363.04; 600/427

(58) Field of Classification Search
USPC .......... 378/65; 600/427; 250/363.02, 363.03, 250/363.04
See application file for complete search history.

(56) References Cited

U.S. PATENT DOCUMENTS

| | | | | |
|---|---|---|---|---|
| 5,552,605 | A * | 9/1996 | Arata | 250/363.04 |
| 5,901,199 | A * | 5/1999 | Murphy et al. | 378/65 |
| 6,298,260 | B1 | 10/2001 | Sontag et al. | |
| 6,339,652 | B1 * | 1/2002 | Hawkins et al. | 382/131 |
| 6,980,683 | B2 * | 12/2005 | Jones | 382/131 |

(Continued)

FOREIGN PATENT DOCUMENTS

| | | |
|---|---|---|
| EP | 1520516 A1 | 4/2005 |
| WO | 9903397 A1 | 1/1999 |

(Continued)

OTHER PUBLICATIONS

Kubo, et al., Respiration gated radiotherapy treatment: a technical study, Phys. Med. Biol., 1996, pp. 83-91, vol. 41.

(Continued)

*Primary Examiner* — Allen C. Ho

(57) ABSTRACT

An apparatus includes a diagnostic scanner (102) and a treatment planner (112). The treatment planner (112) plans a treatment to be applied to an object. A treatment device (114) treats the object according to the treatment plan. A treatment scanner (108) scans the object during a treatment session. A motion modeler (116) uses information from the treatment scan to model a motion of the object. A motion compensated quantitative data generator (1004) uses data from the diagnostic (102) or other scanner, as well as feature geometry (1008) and feature motion (1006) information, to generate motion compensated quantitative data indicative of a feature of the object.

19 Claims, 11 Drawing Sheets

(56) References Cited

U.S. PATENT DOCUMENTS

| | | | |
|---|---|---|---|
| 6,990,175 B2* | 1/2006 | Nakashima et al. | 378/65 |
| 7,221,728 B2* | 5/2007 | Edic et al. | 378/8 |
| 7,321,122 B2* | 1/2008 | Bryman | 250/363.03 |
| 7,453,984 B2* | 11/2008 | Chen et al. | 378/65 |
| 7,574,249 B2* | 8/2009 | Piacsek et al. | 600/425 |
| 7,593,558 B2* | 9/2009 | Boese et al. | 382/128 |
| 7,599,540 B2* | 10/2009 | Koehler | 382/130 |
| 7,626,171 B2* | 12/2009 | Cooke et al. | 250/363.03 |
| 7,813,783 B2* | 10/2010 | Thomas et al. | 600/407 |
| 7,923,690 B2* | 4/2011 | Thielemans | 250/363.03 |
| 8,005,284 B2* | 8/2011 | Sakaguchi et al. | 382/131 |
| 8,017,915 B2* | 9/2011 | Mazin | 250/363.04 |
| 8,098,916 B2* | 1/2012 | Thielemans et al. | 382/131 |
| 8,144,962 B2* | 3/2012 | Busch et al. | 382/131 |
| 8,180,432 B2* | 5/2012 | Sayeh | 600/426 |
| 8,331,639 B2* | 12/2012 | Brinks et al. | 382/128 |
| 8,351,571 B2* | 1/2013 | Brinks et al. | 378/65 |
| 8,351,671 B2* | 1/2013 | Busch et al. | 382/131 |
| 2004/0254773 A1 | 12/2004 | Zhang et al. | |
| 2006/0074292 A1 | 4/2006 | Thomson et al. | |
| 2006/0074304 A1 | 4/2006 | Sayeh | |
| 2006/0182326 A1 | 8/2006 | Schildkraut et al. | |

FOREIGN PATENT DOCUMENTS

| | | |
|---|---|---|
| WO | 0007669 A1 | 2/2000 |
| WO | 2005030267 A1 | 4/2005 |
| WO | 2005115544 A1 | 12/2005 |
| WO | 2007007276 A2 | 1/2007 |

OTHER PUBLICATIONS

Jacobs, et al., A fast algorithm to calculate the exact radiological path through a pixel or voxel space, Journal of computing and information technology, 1998, 12 pages, vol. 6, No. 1., University Computing Center, Zagreb, Croatie.

Minohara, et al., Respiratory gated irradiation system for heavy-ion radiotherapy, Int. J. Radiation Oncology Biol. Phys., 2000, pp. 1097-1103, vol. 47, No. 4, Elsevier Science, Inc.

Parodi, et al., Potential application of PET in quality assurance of proton therapy, Phys. Med. Biol., 2000, pp. N151-N156, vol. 45.

Langen et al., Organ motion and its management, Int. J. Radiation Oncology Biol. Phys., 2001, pp. 265-278, vol. 50, No. 1, Elsevier Science, Inc.

Grozinger, Volume conformal irradiation of moving target volumes with scanned ion beams, dissertation, Technischen Universitat Darmstade, 2004, 191 pages.

Lambert, et al., Intrafractional motion during proton beam scanning, Phys. Med. Biol. 2005, pp. 4853-4862, vol. 50, Institute of Physics Publishing.

Paganetti, et al., Proton beam radiotherapy—the state of the art, New Technologies in Radiation Oncology (Medical Radiology Series), Oct. 2005, 26 pages.

Grozinger, et al., Simulations to design an online motion compensation system for scanned particle beams, Phys. Med. Biol., 2006, pp. 3517-3531, vol. 51, Institute of Physics Publishing.

Jarritt, et al., The role of PET/CT scanning in radiotherapy planning, The British Journal of Radiology, Special Issue, 2006, pp. 527-535, vol. 79.

Varian Medical Systems, On-board imager kv imaging system, published on or before download date Jan. 25, 2007, 2 pages, http://www.varian.com/orad/prd172.html.

Calypso Medical, Calypso 4D localization system—GPS for the body, published on or before the download date Jan. 25, 2007, 2 pages, http://www.calypsomedical.com/products/default.asp.

* cited by examiner

MOTION COMPENSATION IN QUANTITATIVE DATA ANALYSIS AND THERAPY

CROSS REFERENCE TO RELATED APPLICATIONS

This application claims the benefit of U.S. provisional application Ser. No. 60/888,561 filed Feb. 7, 2007, which is incorporated herein by reference.

The present application relates to motion tracking in connection with the application of a treatment to an object. It also relates to quantification of image data acquired from a moving object. It finds particular application to the quantification of positron emission tomography (PET) data. It also finds particular application to the use of PET data to provide real time tracking of subject motion in connection with the application of a medical therapy.

Surgery, chemotherapy, and radiation therapy have traditionally been the three main treatment options in medical oncology. In the case of radiation therapy, intensity modulated radiation therapy (IMRT) devices have gained widespread acceptance as a treatment option. More recently, particle therapy using particles such as protons or ions has attracted attention. The principle behind radiation and particle therapy has been to induce the death of a tumor or other lesion by the localized deposition of energy, while minimizing the dose applied, and thus the damage, to surrounding healthy tissues.

Advances in medical imaging and treatment planning techniques have also led to the development of spatially varying treatment plans. Thus, the treatment plan can be more closely tailored to the requirements of a particular situation, for example by applying relatively higher dose to relatively more aggressive or dose-resistant regions of the lesion.

In the case of a relatively motionless or otherwise static lesion, therapy delivery systems can typically deliver the desired dose with relatively high spatial accuracy. Unfortunately, however, motion such as periodic respiratory or cardiac motion can cause the lesion to present a moving target. To compensate for the effects of such motion, and to ensure that the clinical target volume receives the desired dose, a planning margin has been established, with the dose applied to the relatively larger volume. Unfortunately, however, such an approach can be injurious to otherwise healthy tissue. Moreover, such motion also tends to reduce the accuracy with which a spatially varying dose can be applied to the desired regions of the tumor.

Several approaches for handling intra-fractional motion (i.e., motion occurring during the delivery of a particular treatment fraction) have been described. In a respiratory gated delivery, the dose delivery has been gated according to the measured respiratory phase (e.g., so that dose delivery is limited to time periods that correspond to full expiration). In another technique, an x-ray tube and flat panel x-ray detector have been mounted in a known physical relation to a linear accelerator, with the detector yielding images showing internal anatomic landmarks. The detector can also track anatomic motion and thus provide an indication of how the tumor will move during the treatment due to physiological processes such as respiration. In another approach, electromagnetic transponders have been implanted in or near the treatment site. The transponder signals are detected by a localizer, and the position information is used to generate location instructions to a therapist for registering the patient's treatment target to isocenter prior to treatment. It has also been proposed to use the localization information to identify shifts of the target from its prescribed location during the treatment, with real time graphs highlighting shifts in position that exceed a pre-determined threshold.

Each of the foregoing techniques presents various drawbacks. For example, a gated dose delivery can result in extended treatment times. Moreover, the spatial accuracy of such an approach depends on the accuracy with which the location and motion of the target region can be estimated. Spatial accuracy is also reduced where the position of the target varies from one respiratory cycle to the next. The x-ray detector based technique requires the application of a generalized, non-therapeutic x-ray dose, and also depends on the ability to identify suitable anatomical landmarks, the position and motion of which may differ from that of the target lesion. The transponder based technique requires an invasive implantation procedure, and likewise depends on the ability to implant the transponders at a location whose position and motion correspond to that of the target location.

While the above discussion has focused on the accuracy with which a desired treatment is delivered, the identification and selection of an appropriate treatment can also be an important consideration. In PET imaging, the mean standard uptake value (SUV) has been used to provide a quantitative assessment of a suspected pathology or other feature of interest. As the SUV, along with other quantitative and qualitative information, can influence the assessment of a pathology or other feature of interest (e.g., an assessment of whether a tumor is malignant or benign) and/or the selection of an appropriate course of treatment, it is generally desirable to provide the clinician or other user with relatively accurate SUV information.

The mean SUV is ordinarily calculated as a function of factors such as the measured activity of the feature, the applied radionuclide dose, and the patient weight. Due to the statistical nature of underlying radioactive decay, the activity as measured at a given voxel can be relatively noisy, thus leading to variations in the calculated SUV. To reduce the effect of these variations, voxels belonging to the same anatomical or morphological structure have been combined to yield a relatively larger region of interest (ROI). The activity over the larger ROI is then used to calculate the SUV. Unfortunately, motion of the larger ROI during the image acquisition can degrade the accuracy of the activity measurement, thereby reducing the accuracy of the SUV calculation.

Aspects of the present application address these matters and others.

In accordance with one aspect of the present application, an apparatus includes a scanner that acquires projection data indicative of an object, with the object including a treatment target that is subject to motion during a treatment session. The apparatus also includes a motion modeler that uses projection data acquired during the treatment session to model the motion of the target and a treatment device that treats the target during the treatment session. The treatment device varies a spatial location of the applied treatment as a function of the motion model.

In accordance with another aspect, a computer readable storage medium contains instructions which, when executed by a processor, cause the processor to carry out a method. The method includes selecting projection data indicative of radionuclide decays occurring in a region of interest of an object during a treatment session in which a treatment is applied to a moving target of the object, using the selected projection data to identify a characteristic feature of the region of interest, modeling the motion of the characteristic feature, and repeating the steps of selecting, using the selected projection data, and modeling a plurality of times during the treatment session.

According to another aspect, a method includes generating image data of an object and using the generated image data to identify a region of interest of the object, with the motion of the region of interest being indicative of the motion of a target. The method also includes selecting raw data acquired in an imaging examination of the object that is indicative of the region of interest, using the selected raw data to model a motion of the target, adjusting, as a function of the motion model, a characteristic of a treatment for application to the target, and repeating the steps of selecting, using the selected raw data, and adjusting in substantially real time during a treatment session so as to adjust the characteristic in coordination with the motion of the target.

According to another aspect, a motion tracking apparatus includes means for acquiring raw data indicative of radionuclide decays in a subject during a treatment session in which a treatment is applied to a lesion of the subject, the lesion being subject to periodic physiological motion. The apparatus also includes means for processing the raw data to track the motion of a characteristic feature of the lesion in three spatial dimensions in substantially real time during the treatment session.

According to another aspect, an apparatus includes a motion compensated quantitative data generator that uses spatially varying activity data representative of radionuclide decays detected during an examination of an object and a motion compensation function to generate quantitative data indicative of the object. The motion compensation function compensates for a motion artifact induced error in a calculation that uses the activity data to generate the quantitative data.

According to another aspect, a computer readable storage medium contains instructions which, when executed by a computer, cause the computer to carry out a method. The method includes using spatially varying activity data representative of radiation decays in an object to generate motion compensated quantitative data indicative of a feature of the object. The step of using includes applying a motion compensation function that compensates for an error introduced by a motion artifact in the spatially varying activity data.

According to another aspect, a method includes using spatially varying activity data representative of radionuclide decays to generate quantitative data indicative of a pathology of a subject, and adjusting the quantitative data according to a motion compensation function that compensates for an error introduced by a motion artifact in the spatially varying activity data.

According to another aspect, a method includes presenting first image data indicative of an object to a human user. The image data includes a plurality of features. The method also includes selecting a first feature, generating quantitative data indicative of the first feature, selecting a second feature, and performing a motion compensated reconstruction that compensates for a motion of the second feature.

According to another aspect, an apparatus includes means for presenting first image data indicative of an object to a human user. The image data includes a plurality of features. The apparatus also includes means for selecting a first feature, means for generating quantitative data indicative of the first feature, means for selecting a second feature, and means for performing a motion compensated reconstruction that compensates for a motion of the second feature.

According to another aspect, a motion compensated quantitative data generator uses data representative of a spatial distribution of radionuclide decays in an object to generate motion compensated quantitative data. The quantitative data generator applies a motion compensation to compensate for a motion artifact in the data representative of the spatial distribution.

Still further aspects of the present application will be appreciated by those of ordinary skill in the art upon reading and understand the following detailed description.

The invention may take form in various components and arrangements of components, and in various steps and arrangements of steps. The drawings are only for purposes of illustrating the preferred embodiments and are not to be construed as limiting the invention.

Figure 1:
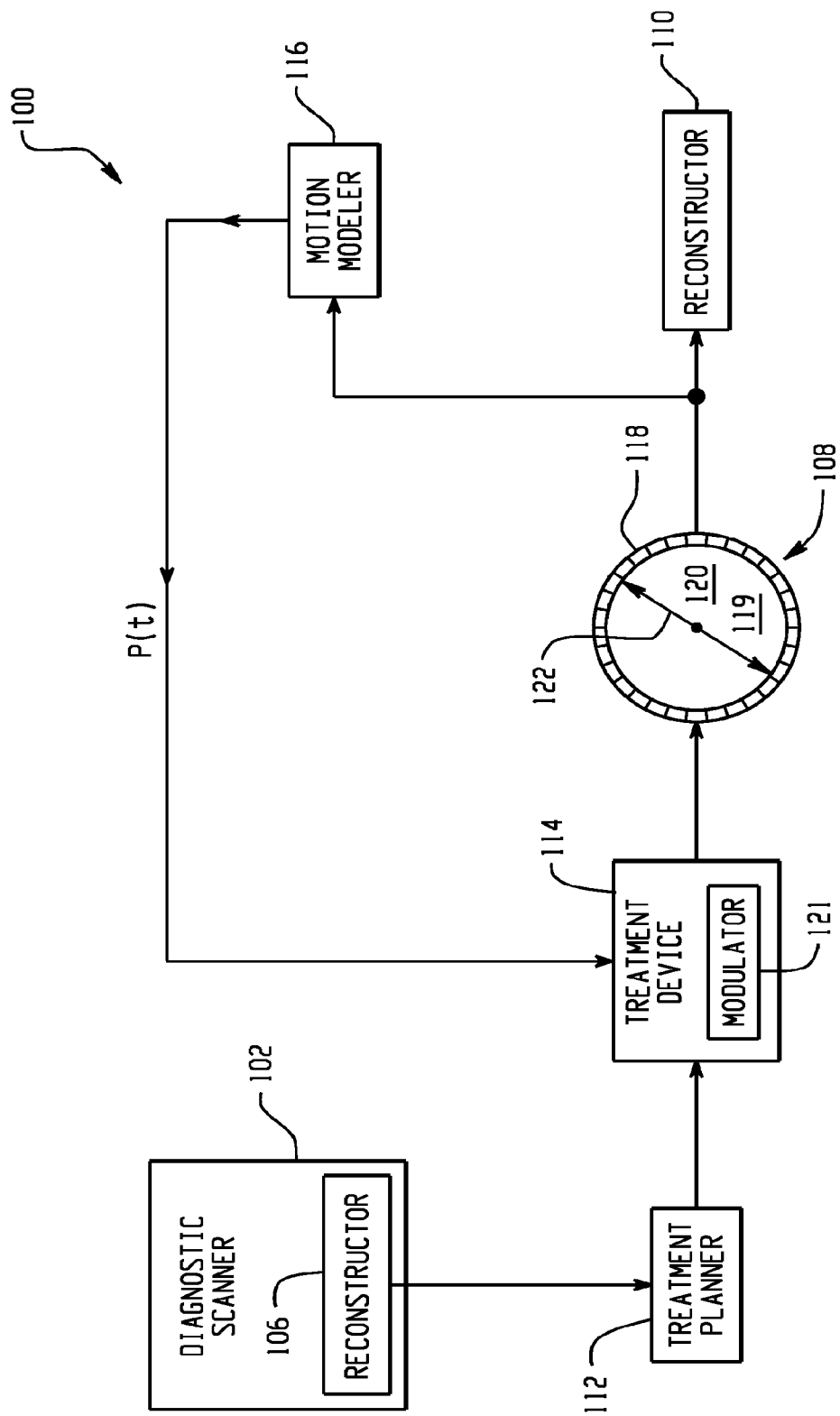
FIG. 1 is a block diagram of a diagnosis and treatment system.

With reference to FIG. 1, a system 100 includes a first or diagnostic scanner 102, a treatment planner 112, a treatment device 114, and a second or treatment scanner 108.

The first scanner 102 provides image data indicative of an interior of an object under examination, with the scanner modality being selected based on factors such as characteristics of the object being imaged, the region to be imaged and/or treated, and the like. Examples of suitable scanners include positron emission tomography (PET), single photon emission tomography (SPECT), and functional magnetic resonance imaging (fMRI) scanners that provide functional information about the object, as well as computed tomography (CT), MRI, ultrasound (US) or scanners which provide information about the structure of the object. Where information from more than one modality is desired, multiple scanners may be provided. Hybrid scanners such as combined PET/CT, SPECT/CT, and PET/MR scanners are also contemplated.

As illustrated, the first scanner 102 includes a reconstructor 106 that reconstructs the raw or projection data generated in the course of an imaging examination using analytical, iterative, or other suitable reconstruction techniques to generate volumetric or image space data indicative of the object under examination. Where the first scanner 102 includes more than one modality, more than one reconstructor 106 may also be provided. In one implementation, the first scanner 102 and reconstructor 106 cooperate to generate diagnostic quality images.

The treatment planner 112 uses the image data from the first scanner 102 and/or other relevant information to plan a treatment to be applied to a treatment target. In the case of a radiation treatment planning (RTP) system used in radiation oncology, for example, the treatment plan typically includes a spatially varying radiation dose that is to be applied to a tumor or other lesion.

As illustrated in FIG. 1, the treatment scanner 108 is a PET scanner. PET scanners conventionally include a plurality of radiation sensitive detectors 118 disposed about an examination region 120 in a generally ring or cylindrically shaped arrangement. In connection with a PET examination, a tracer that includes a positron emitting radionuclide is introduced into the object under examination. As the radionuclide decays, the emitted positrons interact with electrons in what are known as positron annihilations, with the annihilations generating pairs of temporally coincident 511 kiloelectron volt (keV) gamma rays which travel in substantially opposite directions along a line of response (LOR) 122. Where the scanner 108 is a time of flight (TOF) PET scanner, a time of flight detector measures the arrival times of the coincident photons, with the resultant information being used to estimate the position of the annihilation along the LOR 122.

The treatment scanner 108 operates in coordination with the treatment device 114 to generate raw or projection data indicative of annihilations detected during the course of a treatment session or fraction. In the case of a list mode acquisition, the data includes a list of the many annihilations detected in the course of a given scan, with the entries in the list typically containing information indicative of the location and orientation of the LOR 122, the location of the event along the LOR 122 (particularly in the case of a TOF system), the time at which the annihilation was detected, and other relevant information. Note that, where the projection data is used primarily for motion tracking, the projection data produced by the scanner 108 may be of a quality insufficient to produce diagnostic images.

A reconstructor 110 may be provided to reconstruct the raw data using a suitable iterative, analytical, or other reconstruction technique and hence generate volumetric image data indicative of the object, for example for display in a human perceptible form via a monitor, films, or the like.

As will be described further below, the motion modeler 116 uses projection data acquired by the treatment scanner 108 during a treatment session otherwise during application of the treatment by the treatment device 114 to track the motion of the treatment target. More specifically, the motion tracking is preferably performed in substantially real time so as to track the target over the course of the treatment session.

Where the motion is modeled in three spatial dimensions, the motion track or model can be expressed according to the relation:

$$P(t)=(x(t),y(t),z(t)) \quad \text{Equation 1}$$

where P(t) is position of the target or other region of interest as a function of time, and x(t), y(t), and z(t) represent the position of the region of interest along respective x, y, and z axes. The motion model may also be expressed other than in terms of absolute position (e.g., in terms of positional differences, velocities, accelerations or the like) and in relation to other desired coordinate systems.

The treatment device 114, which is situated relative to the scanner so that its treatment region 119 at least partially corresponds to the examination region 120, uses information from the treatment planner 112 and the motion modeler 116 to apply the desired treatment to the object. More specifically, the treatment device 114 uses motion information from the motion model P(t) to compensate for motion of the treatment target in substantially real time during the course of the applied treatment.

As illustrated in FIG. 1, the treatment device 114 includes a modulator 121 which modulates an intensity or other characteristic of the treatment applied to the object, for example by modulating a spatial, temporal, and/or other characteristic of the applied dose so that the applied treatment approximates that calculated by treatment planner 112.

Again in relation to the example of external radiation therapy in oncology, the treatment device 114 may include an intensity modulated radiation therapy device. Such devices typically include a multi-leaf collimator which is used to modulate the applied radiation so as to apply the desired radiation dose to the tumor. Other treatment devices, including but not limited to linear accelerators, particle therapy devices, radio frequency ablation or other devices, and high field ultrasound treatment devices are also contemplated.

The object is registered or otherwise positioned in the respective treatment regions 119, 120 of the treatment device 114 and the treatment scanner 108 in connection with an applied treatment which, in the case of a fractionated therapy, may be one of a plurality of treatment sessions. Depending on the object to be treated and the nature of the treatment, such positioning may be facilitated by way of fiducial markers, positioning devices which conform to a portion of the object (e.g., a conformal face mask in the case of a therapy to be applied to the head of a human patient), other restraints, or other suitable techniques. Information from the motion model P(t) may also be used, either alone in conjunction with other positioning aids, to suitably position the patient in connection with the treatment Turning now to FIG. 2, the motion modeler 116 includes a grouper 252, filter 254, a characteristic processor 258, and a position determiner 282. As noted above, the motion modeler 116 receives the raw or projection data from the treatment scanner 108 in substantially real time as the data is acquired in the course of a scan.

The grouper 252 groups the projection data from the treatment scanner 108 into temporal groups. Where the data includes list mode PET data, for example, the grouper 252 groups the various LORs into temporal groups, with the duration of the groups ordinarily being established as a function of factors such as the nature and rate of the motion being modeled, the desired temporal resolution, the annihilation count rate, the speed of the motion modeler 116, and the rate at which the treatment device 114 can steer or otherwise modulate the applied therapy. In one implementation, the groups each have the same temporal duration, with the number of LORs varying from group to group. In another, each group contains the same number of LORs, with the temporal duration varying from group to group. In another, both the temporal duration and the number of LORs are allowed to vary, within limits.

The filter 254 filters or disregards projection data that does not intersect (or stated conversely, selects projection data which does intersect) a user or automatically determined region of interest (ROI) which preferably includes the target. Again in example of PET data in an oncology application, the filter 254 selects those LORs which intersect an ROI which includes a tumor being treated. Where TOP data is available, those LORs for which the annihilation likely falls outside the ROI may be discarded.

Figure 2:
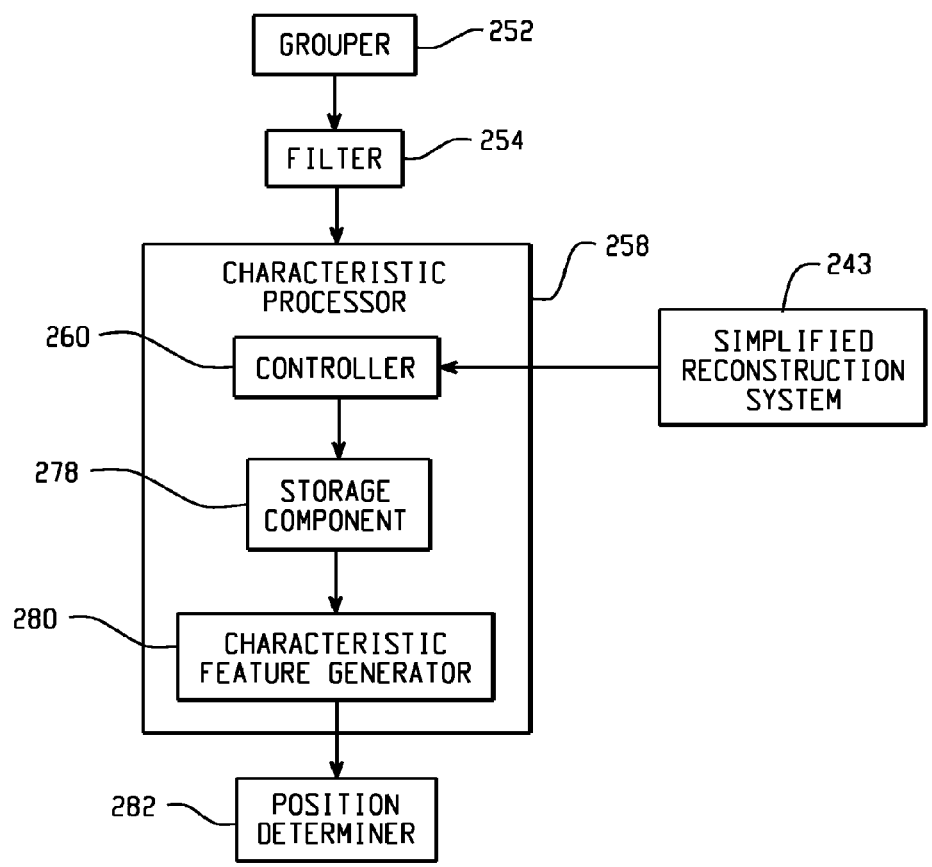
FIG. 2 is a block diagram of a motion modeler.

A characteristic processor 258 determines a characteristic feature such as a center of mass or other center function of the projection data of the filtered group. As shown in the example of FIG. 2, a controller 260 of the characteristic processor 258 accesses a simplified reconstruction system 243. The simplified reconstructor 243 performs a locally constrained back-projection of the various groups of filtered projection data to generate a partial image corresponding to the temporal group. The partial image is stored in a storage component 278 such as a memory.

Figure 4:
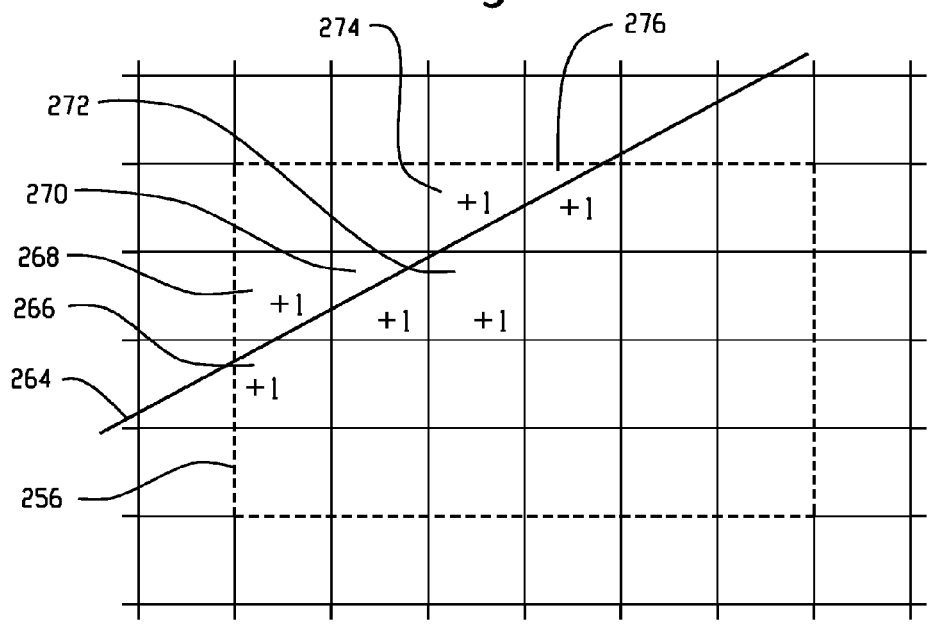
FIG. 4 depicts aspects of a technique for generating intermediate images.

In one implementation, the distance over which the various projections intersect the voxels of the ROI 256 is calculated, with the simplified reconstructor 243 updating the voxel values as a function of the calculated distance. In a simplified and hence relatively faster implementation, the value of a given voxel is incremented or otherwise increased uniformly each time a projection intersects the voxel. This is illustrated in FIG. 4 again in the example case of a PET system where an LOR 264 intersects voxels 266, 268, 270, 272, 274, and 276 of the ROI 256. Note that the voxel weighting produced by the simplified reconstructor 243 may also take into account TOF data, if available.

Returning to FIG. 2, a characteristic feature generator 280 computes a center of mass, center of activity, or other characteristic feature of a partial image. Depending on the selected simplified reconstruction technique, and to reduce the effects of projection data indicative of regions outside the ROI 256, it may be desirable to consider only a subset of the voxels in the ROI when calculating the characteristic feature. This may be accomplished, for example, by way of a thresholding technique in which those voxels having a value less than a user selected or other desired percentage of the maximum voxel value of the ROI are not considered.

The motion determiner 282 uses the characteristic feature data to generate the motion model P(t), with the motion model being stored in a computer readable memory accessible to or otherwise provided to the treatment device 114. Note that the motion determiner 282 may also use motion data to predict a future position or motion of the lesion, for example by performing a first or higher order extrapolation using one or more past motion measurements. As will be appreciated, the process is repeated in substantially real time from each of a plurality of temporal groups acquired during the course of a scan.

Figure 3:
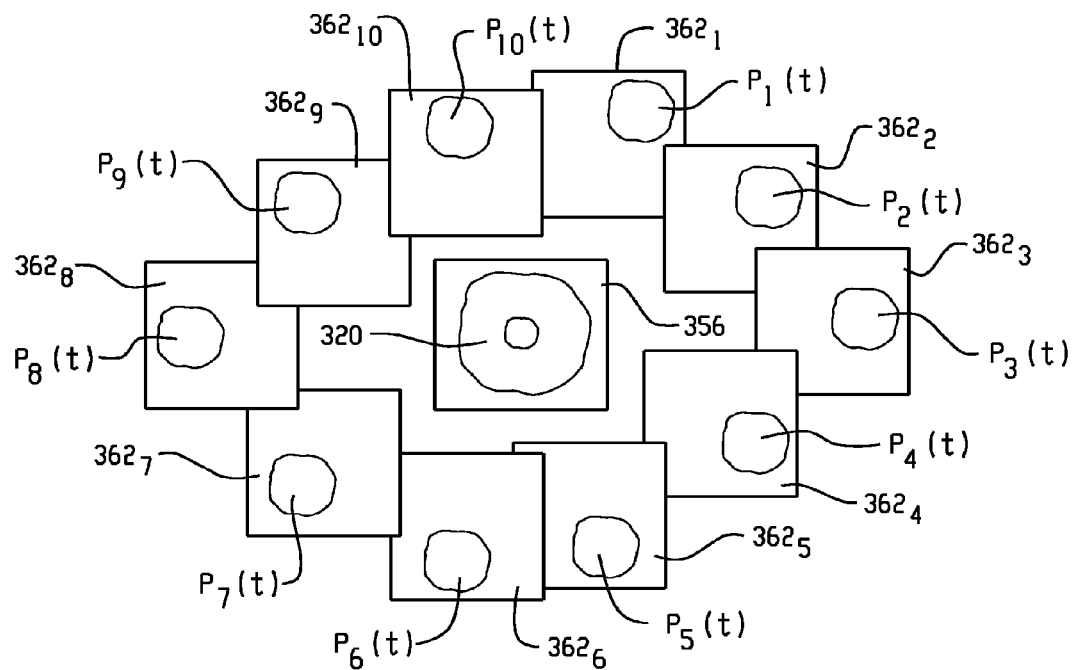
FIG. 3 depicts intermediate images.

FIG. 3 depicts one example of an ROI 356 and a plurality of intermediate images $362_{1-10}$ generated by the simplified reconstructor 243 in connection with ten (10) successive temporal groups, it being understood that a motion model $P_n(t)$ would ordinarily be generated for each group. In the example of FIG. 3, a tumor 320 undergoes a generally circular, clockwise motion in the ROI 356. While ten (10) intermediate images 362 and motion models $P_n(t)$ are shown in FIG. 3 for the purposes of illustration, other numbers of temporal groups and/or intermediate images may also be generated. It will also be appreciated that FIG. 3 depicts an image slice of the ROI 356. Where the ROI 356 includes a volume, intermediate images covering the volume would be reconstructed.

Figure 6:
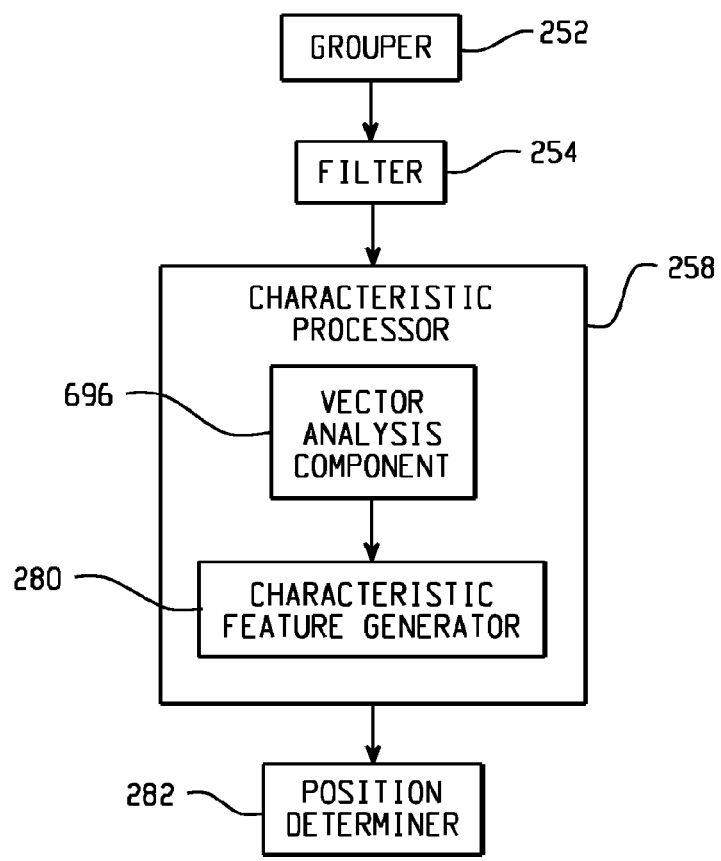
FIG. 6 is a block diagram of a motion modeler.

FIG. 6 depicts an alternative embodiment of the motion modeler 116, with like reference numerals describing items analogous to those described above in relation to FIG. 2.

As illustrated, the characteristic processor 258 includes a vector analysis component 696 which receives the filtered projection data generated by the filter 254. Again in the context of LORs generated in PET imaging, it will be assumed that each LOR can be described by a point $\vec{P}_x$ on the LOR and a unit vector $\vec{p}_x$ which describes its direction.

Returning to FIG. 6, the vector analysis component 696 generates a collection of points {C1, C2, . . . Cn} for n successive pairs of LORs, thereby generating a point cloud.

Note that parallel LORs or LORs perpendicular to the x-axis are treated separately.

The characteristic feature generator 280 determines the center or mass or other desired characteristic feature of the point cloud. If desired, outlying points may be disregarded when determining the center of mass. The motion determiner 282 again uses the characteristic feature data to generate the motion model P(t).

Suitable techniques for determining a motion of a region of interest are also disclosed in commonly owned U.S. Pat. No. 8,144,962 filed on Feb. 28, 2006 and entitled Local Motion Compensation Based on List Mode Data, which application is expressly incorporated by reference in its entirety herein. The motion model P(t) may also be used by the reconstructor 110 to compensate for motion in a reconstructed image. In the case of data from a PET scanner, for example, the motion model P(t) can be used to shift the positions of LORs indicative of events occurring in the ROI so as to compensate for the detected motion. All or a desired portion of the acquired data set is then reconstructed.

Variations are contemplated. While the first 102 and second 108 scanners have been described as separate devices, they may also be one and the same device. The second scanner 108 is not limited to a PET scanner, and may be a SPECT or other modality scanner, a hybrid modality scanner, or the like. The techniques described above are also applicable to medical applications other than oncology and to industrial or other non-medical applications which it is desired to apply a treatment to a moving object.

Note also that some or all of the functionality described above may be combined into a single device, or divided among multiple devices. For example, some or all of the motion modeler 116 may be implemented as part of the scanner 108; the reconstructors 106, 110 may be implemented other than as part of the scanners 102, 108. As will also be appreciated by those of ordinary skill in the art, the various techniques described above may be implemented by way of computer readable instructions stored on suitable computer readable media. When executed by a computer processor, the instructions cause the computer processor to carry out the described techniques.

The techniques described above may also be applied to acquisitions in which the raw or projection data is sorted or binned into a plurality of bins. In such an implementation, the grouper 252 would operate at the time of or in connection with the data acquisition so as to acquire rebinned data corresponding the desired time periods.

There may also be situations in which it is relatively difficult to effectively identify a specific lesion or other feature of the object in order to establish the motion model. For example, the lesion or other target may be blurred by motion of the object, with such blurring tending to reduce the average intensity of the hot spot. The reduction in intensity may potentially lead to the non-identification of the lesion or otherwise complicate its detection. Consequently, a motion correction may be applied to a region known to have or suspected of containing the lesion. As the motion correction tends to intensify the relatively weaker areas and thus aid in the identification of suspect regions, the motion corrected data may be analyzed to identify the desired target region.

The ROI may also be established at a second or motion ROI, the motion of which serves as a suitable proxy for that of the target. Such an arrangement is particularly well suited to situations in which a tracer having an affinity for the target produces a relatively low intensity hot spot, the tracer has an affinity for the second ROI or where the treatment scanner 108 is of a modality which is not particularly well suited for imaging the target.

Figure 5:
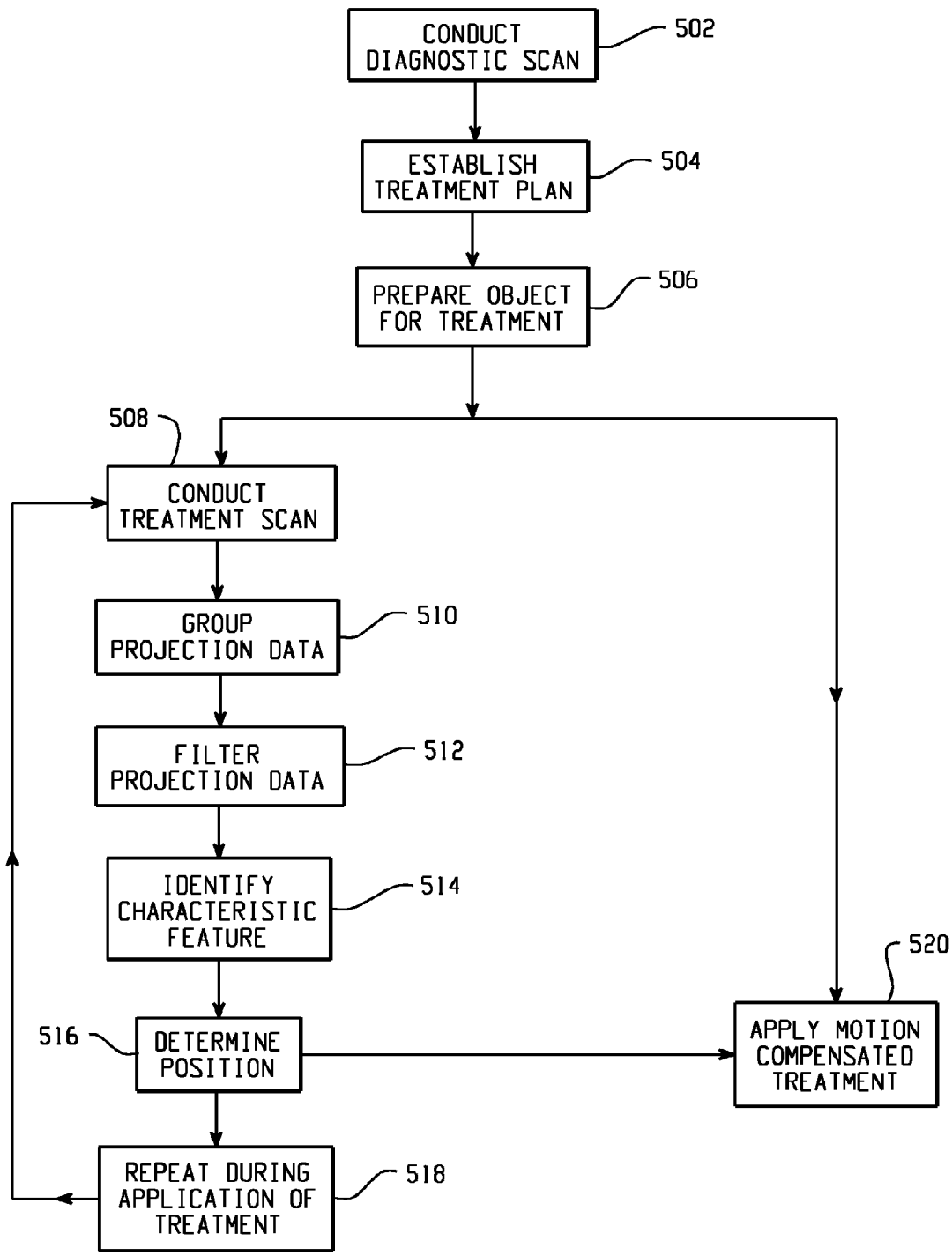
FIG. 5 depicts a motion tracking method.

Operation will now be described in relation to FIG. 5.

A diagnostic scan is obtained at 502, and a treatment plan is established at 504.

The object is prepared for treatment at 506. A tracer having an affinity for the target is introduced into the object. Again in the example of a PET scanner in medical oncology, a tracer such as FDG indicative of the relatively higher metabolic rate of cancerous lesions is introduced into the anatomy of a patient. The patient is also positioned so that the target is suitably positioned in the treatment 119 and examination 120 regions. In this regard, the treatment scanner 108 may be used to conduct an initial scan of the object, with the resultant image data used to assist in the positioning of the object and/or to determine the ROI.

As will be appreciated, the target may be subject to gross, periodic, or other motion over the course of the applied treatment. Again to the example of a human patient, the motion may be due to periodic physiological motion such as respiratory or cardiac motion, gross patient motion, position shifts caused by physiological processes such as the filling of the bladder or colon, or other causes.

A treatment scan is conducted at 508. The projection data is temporally grouped at 510, the grouped data is filtered at 512, the characteristic feature is identified at 514, and the position of the characteristic feature is determined at 516. As indicated at 518, steps 508 through 516 are repeated in substantially real time during the course of the treatment session.

The motion compensated treatment applied at 520, with the determined position of the characteristic feature being used to compensate for the motion of the target, for example by steering or gating the applied particle or photon beam or other applied treatment in temporal coordination with the determined position of the characteristic feature. While the treatment is applied and the treatment scan is conducted temporally concurrently (i.e., with the object suitably positioned for examination and treatment), it will be appreciated that, the image acquisition and treatment application may be gated so that the time periods during which the acquisition and treatment are conducted are mutually exclusive, partially overlapping, or the like.

Returning briefly to FIG. 1, the treatment planner 112 uses image data from the scanner 102 and/or other relevant information to develop a desired treatment. In PET or SPECT scanner, for example, the information may include quantitative data such as a mean SUV that is calculated as a function of a measured activity. An example mean SUV calculation can be expressed as follows:

$$SUV_{mean} = \frac{1}{|V_{ROI}|} \int_{V_{ROI}} \alpha_m(x) dV, \quad \text{Equation 6}$$

where $V_{ROI}$ is the set of voxels belonging to an ROI over which the SUV is calculated, $|V_{ROI}|$ is the associated volume measure, and $\alpha_m(x)$ is the measured activity at position x in the volume or image space. Note that other factors such as radionuclide dose, patient weight, and the like that are ordinarily included in the SUV calculation have been omitted from Equation 6 for clarity of explanation and can readily be incorporated by those of ordinary skill in the art.

Equation 6 can be rewritten as follows:

$$S = \frac{1}{|V_{ROI}|} \int_{V_{ROI}} a(x) dV \quad \text{Equation 7}$$

where a(x) is the temporal mean of the measured activity $\alpha_m$ at position x during a measurement time T:

$$a(x) = \frac{1}{T} \int_0^T \alpha(x, t) dt. \quad \text{Equation 8}$$

Figure 7:
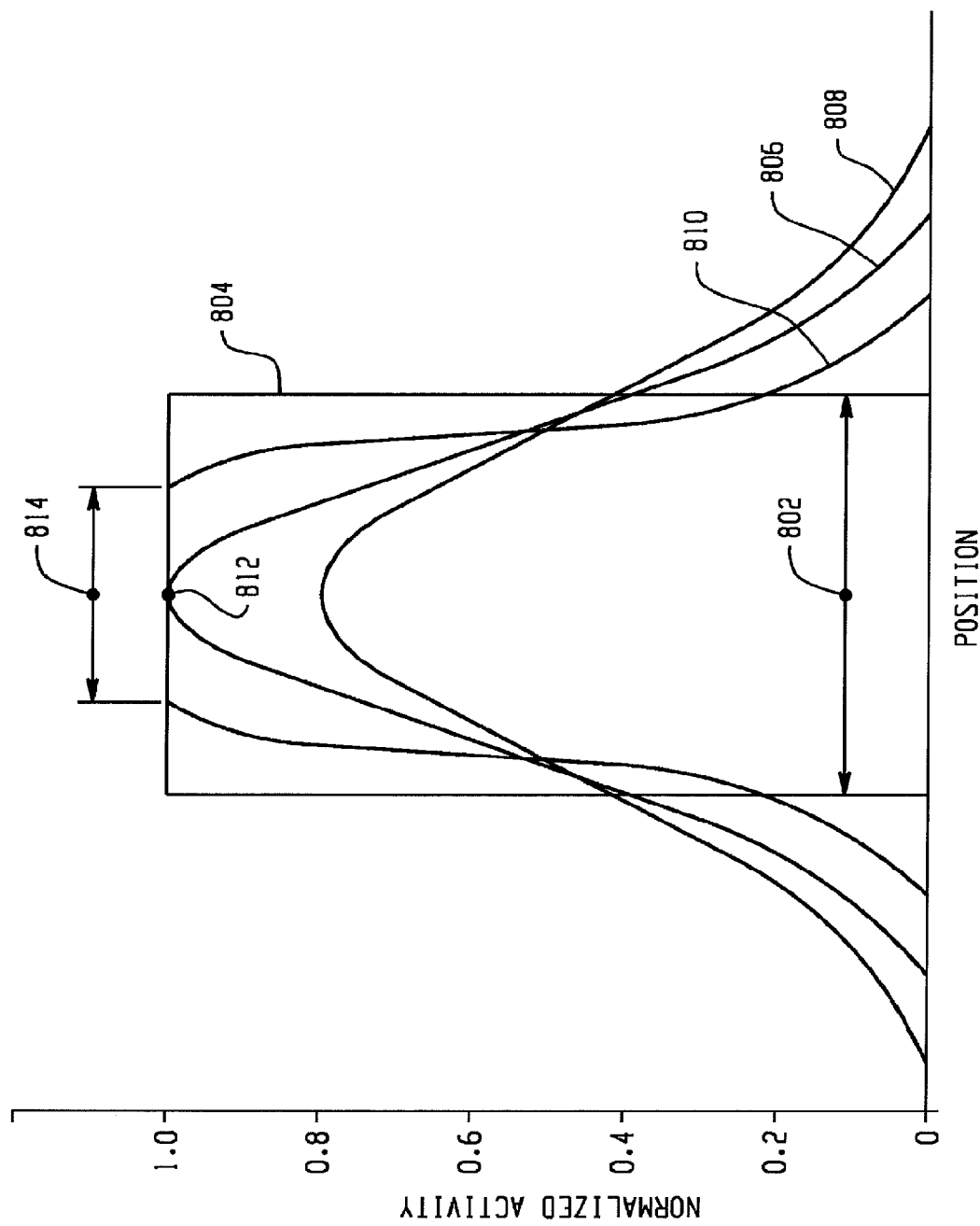
FIG. 7 depicts an effect of motion on a measured activity.

Turning now to FIG. 7, motion occurring during the data acquisition can lead to inaccuracies in the activity measurement and an underestimation of the SUV. In FIG. 7, the abscissa or x-axis depicts the position or location x in an image or measurement space, while the ordinate or y-axis depicts a normalized activity measurement. For the purposes of the present explanation, it will be assumed that a feature of interest such as a lesion has a dimension 802 and a normalized activity $\alpha(x)=1$ that is uniform over its volume.

Curve 804 depicts the measured activity $\alpha_m(x)$ in a case where the lesion is stationary, and with other error sources being neglected for clarity of explanation. As illustrated by profiles 806, 808, 810, however, the activity measurement $\alpha_m(x)$ will be influenced by lesion motion. Profile 806 illustrates a first situation in which the amplitude of the motion is equal to the dimension 802. As can be seen, the measured activity $\alpha_m(x)$ is equal to the actual activity $\alpha(x)$ at a point 812. Profile 808 illustrates a second situation in which the amplitude of the motion is greater than the dimension 802 of the lesion. As can be seen, the peak value of the measured activity $\alpha_m(x)$ is less than the actual activity $\alpha(x)$. Profile 810 illustrates a third situation in which the amplitude of the motion is less than the dimension of the lesion. As can be seen, the measured activity $\alpha_m(x)$ corresponds to the actual activity $\alpha(x)$ for a range of locations 814.

These variations can lead to motion artifacts such as reduced contrast and blurring. In the third situation, for example, the image data may include a central region in which the temporal mean a(x) of the measured activity is substantially correct. However, the dimension of the central region (e.g., the dimension 814) will be underrepresented. In somewhat less central regions (e.g., in regions outside the dimension 814 but inside the dimension 802), the temporal mean a(x) of the measured activity will be lower than the actual activity $\alpha(x)$. In still less central regions (e.g., in regions outside the dimension 802), the measured activity $\alpha(x)$ (and consequently the temporal mean a(x) of the measured activity) will be greater than the actual activity $\alpha(x)$. As will be appreciated from an analysis of the various curves 804, 806, 808, 810, the magnitude of these motion effects will vary as a function of the lesion size and motion characteristics.

Moreover, these motion effects can complicate the identification of an appropriate ROI. Where, for example, the lesion size and motion are as depicted as in curve 810, the SUV will be calculated correctly if the dimension of the ROI is less than or equal to the dimension 814. As the situation approaches that depicted by curve 806 (e.g., if the lesion is relatively smaller and/or the motion is relatively greater), however, the dimension 814 tends to decrease, thus tending to increase the statistical noise in the SUV calculation. If the dimension of the ROI is greater than the dimension 814, on the other hand, the SUV will be underestimated. As the situation approaches that depicted by curve 808, an ROI in which measured activity $\alpha_m(x)$ corresponds to the actual activity $\alpha(x)$ cannot be defined.

Viewed in the context of the various examples of FIG. 7, the calculated mean SUV is the area under the respective curves 804, 806, 808, 810 divided by the dimension of the selected ROE. Again depending on the size and motion of the lesion and the size and location of the selected ROI, calculating the mean SUV according to Equation 6 may underestimate the SUV, as there is some probability that the temporal mean a(x) of the measured activity will be less than the actual value.

Assuming that information about the geometry and the motion of the lesion or other feature of interest is available, motion compensated quantitative data can be generated. A first example of a motion compensated mean SUV calculation will now be described for an example homogeneous sphere having an activity α(x)=1 and a radius r=1 and that undergoes sinusoidal motion having an amplitude A. The position P of the center of the feature can be described as a function of a (normalized) time t∈[0, 1]:

$$P=P(t)=y0+A\sin(2\pi t),\qquad \text{Equation 9}$$

where y0 is the mean position of the sphere.

For the purpose of the present example, it will be assumed that the selected ROI is a sphere having the radius r. The mean SUV calculation of Equation 6 above can be expressed as follows:

$$S = \frac{1}{|V_{ROI}|}\int_0^1 V(t)\,dt \qquad \text{Equation 10}$$

where $|V_{ROI}|$ is the volume of the ROI (i.e., $4\pi r^3/3$ for purposes of the present example) and V(t) is the volume of the intersection of the sphere at position P(t) and the ROI. It will be appreciated that V(t) can readily be calculated for both spherical and/or non-spherical geometries.

The value S from Equation 10 can also be viewed as a motion compensation function that can be applied to an SUV calculated according to Equation 6 and thus generate a motion compensated mean SUV:

$$\text{motion compensated } SUV_{mean} = S^{-1} \cdot \frac{1}{|V_{ROI}|}\int_{V_{ROI}} \alpha_m(x)\,dV. \qquad \text{Equation 11}$$

As an example of the foregoing, it will now be assumed that the feature has a radius r=7 mm and that the amplitude A=10 mm. Note that, in medical imaging, amplitudes of 10 mm are common in lesions near the diaphragm (e.g., lesions present in the lung and liver). In such a case, the mean SUV as calculated according to Equations 6 or 7 above would be underestimated by a factor of about 2.5:

$$SUV_{mean}(r=7\text{ mm}, A=10\text{ mm})=0.395 \qquad \text{Equation 12}$$

Multiplying the mean SUV calculated according to Equations 6 or 7 by a compensation factor of about 2.5 thus yields a motion compensated mean SUV.

Figure 8:
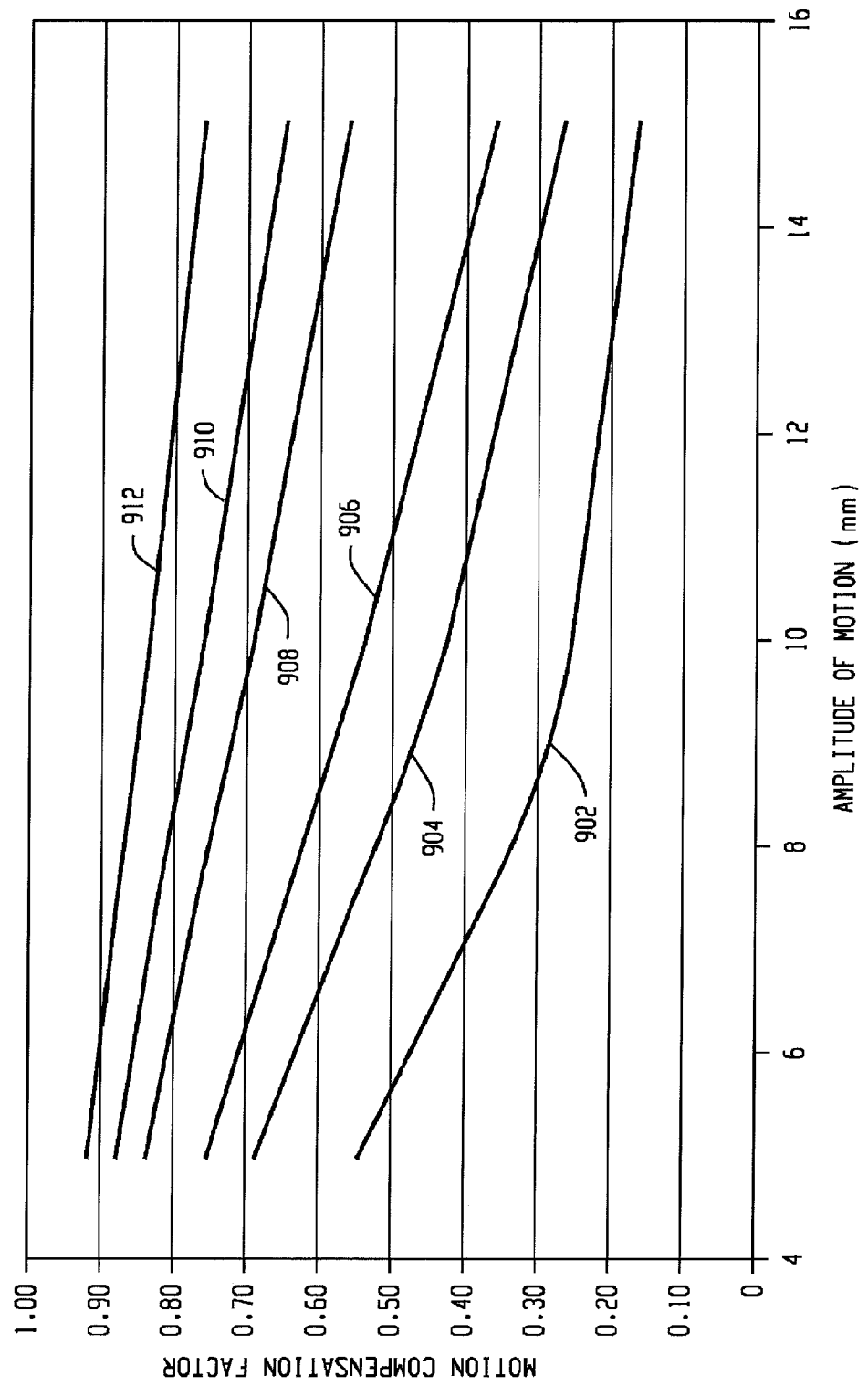
FIG. 8 depicts a motion compensation function.

The foregoing is illustrated more generally with reference to FIG. 8, in which the abscissa depicts the amplitude A of a feature of interest in mm and the ordinate represents the motion compensation function S calculated as described above in Equation 10. The curves 902, 904, 906, 908, 910, 912 illustrate motion compensation functions S generated according to Equation 10 for features of interest having radii of 5, 7.5, 10, 15, 20, and 30 mm respectively. As can be seen, the required motion compensation tends to increase as the motion amplitude A increases and the feature size decreases.

A second example motion compensated mean SUV calculation will now be described. For clarity of explanation, it will be assumed that a lesion or other feature has a uniform activity α, which is approximately true for small lesions. For larger lesions or features having spatially non-uniform activity, the lesion or features can be subdivided into sub-regions in which the activity is substantially uniform.

The activity of the lesion (or sub-region) as measured in a PET, SPECT or other examination be expressed as follows:

$$\Lambda(x)=\alpha\cdot p(x), \qquad \text{Equation 13}$$

where Λ(x) is the measured activity and p(x) is the fraction of the acquisition time during which the activity of the lesion (or sub-region) is at position x. The function p(x), which represents the probability density of the lesion at position x, can be calculated based on the lesion motion and geometry information as described above.

As will be appreciated, the objective is ordinarily to determine the actual activity α. Hence, Equation 13 can be rewritten:

$$\alpha = \frac{\Lambda(x)}{p(x)}. \qquad \text{Equation 14}$$

Viewed from another perspective, then, the probability density p(x) can serve as a spatially varying motion compensation function that compensates for the motion of the lesion during the data acquisition.

By analogy to Equation 11, the motion compensated mean SUV can be calculated as follows:

$$\text{motion compensated } SUV_{mean} = \frac{1}{|V_{ROI}|}\int_{V_{ROI}}\frac{\Lambda(x)}{p(x)}\,dV. \qquad \text{Equation 15}$$

Statistical confidence is improved if the ROI includes the entire region through which the lesion has passed during acquisition:

$$V_{ROI}\!':=\{x|p(x)>0\}. \qquad \text{Equation 16}$$

Variations are possible. For example, the ROI may be truncated to include only the subset $V_{ROI\tau} \subset V_{ROI}$ for which p(x) is greater than a threshold τ:

$$V_{ROI\tau}\!':=\{x|p(x)>\tau\}. \qquad \text{Equation 17}$$

Such an implementation is particularly attractive in situations where the estimated value of the probability density p(x) is relatively unreliable at low values. For lesions or other features that are relatively large in relation to the amplitude, the threshold τ can set at or near 1, in which case the ROI corresponds to the region 814 of FIG. 7.

Figure 9:
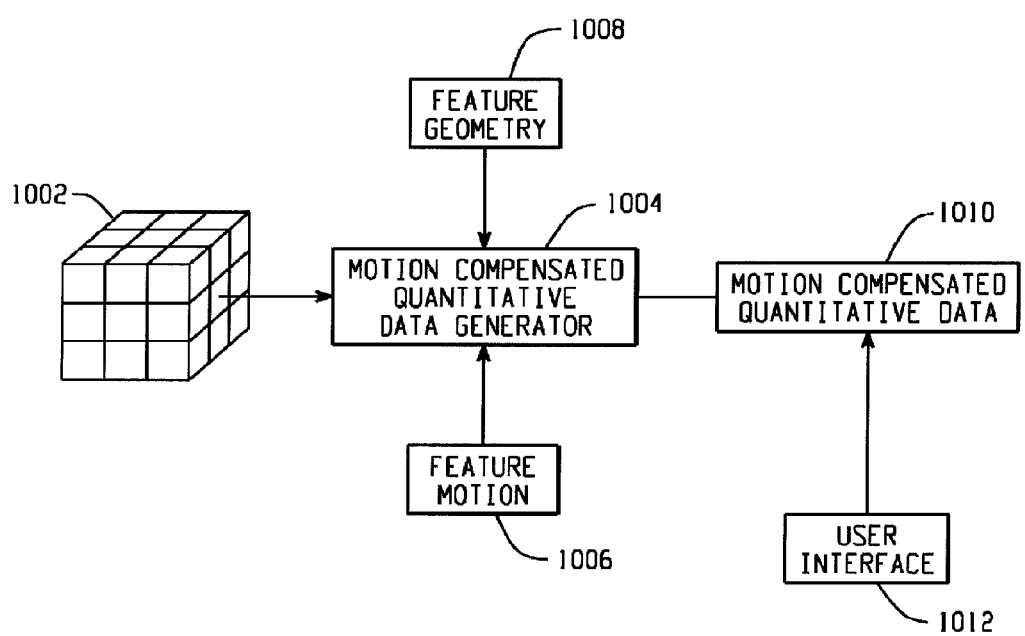
FIG. 9 depicts a motion compensated quantitative data generator.

An apparatus that performs a motion compensated quantitative data calculation will now be described in relation to FIG. 9. As illustrated, a motion compensated quantitative data generator 1004 uses feature geometry information 1008, feature motion information 1006, and spatially varying activity data 1002 representative of radionuclide decays detected during a PET, SPECT, or other examination of an object to generate motion compensated quantitative data 1010 indicative of a feature of the object. As the object may undergo motion during the examination, hence introducing a motion artifact in the spatially varying data, the data generator 1004 compensates for a motion artifact induced error in the calculation of the quantitative data. The motion corrected quantitative data 1010 and/or other relevant information is presented to a human user via a user interface 1012 such as a computer-implemented graphical user interface (GUI).

The feature geometry 1008 may be estimated using information from various sources. As one example, data from an examination of the object conducted using a suitable imaging modality such as CT, MR, US, X-ray, a hybrid imaging modality, or other imaging or non-imaging examination modalities may be used to estimate the size and/or shape of the feature. The feature geometry 1008 may also be estimated from the activity data 1002. Note that the estimation of the feature geometry 1008 may be performed automatically or semi-automatically using a segmentation or other feature detection algorithm, manually by a human user via a user interface such as the user interface 1012, or other suitable estimation techniques.

As another example, a feature simulator may be used to generate a simulated feature having geometric and/or motion characteristics similar to those of a feature present in the activity data 1002. As still another example, the feature geometry 1008 may be estimated based on a priori knowledge of the feature of interest. In oncology, for example, a spherical geometry can provide a reasonable approximation of the shape of a lesion, particularly in the case of smaller lesions. Note that the estimate may also employ information from the various sources in combination.

The feature motion 1006 may likewise be estimated using information from various sources. As one example, the motion 1006 can be estimated by way of motion monitor(s) that are appropriate for the relevant motion. In the medical context, suitable sensors include respiratory, cardiac, and/or other periodic or gross motion monitors. The motion may also be estimated using data from a suitable imaging or other examination of the object, a priori knowledge of the object and its motion characteristics, or the like.

Figure 10A:
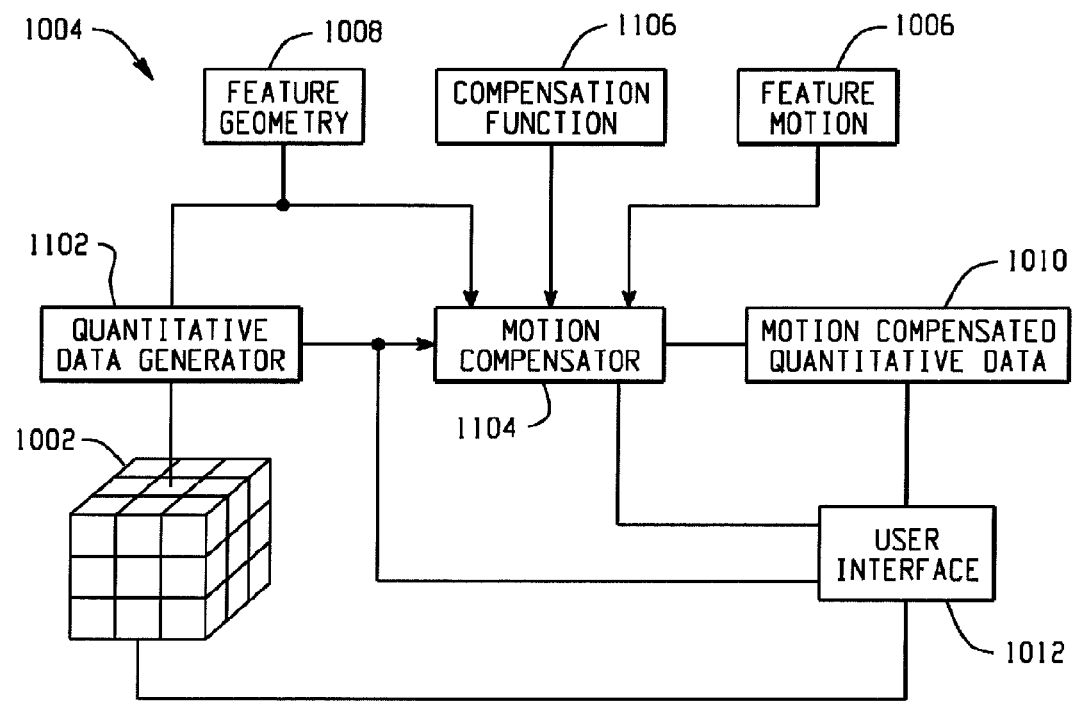
FIG. 10A depicts a motion compensated quantitative data generator.

A first implementation of the motion compensated quantitative data generator 1004 will now be described in relation to FIG. 10A. As illustrated, the motion compensated quantitative data generator includes a quantitative data generator 1102 and a motion compensator 1104. The compensated quantitative data generator 1004 generates quantitative data that may include motion-induced errors. Again in an example where the quantitative data includes a mean SUV, the mean SUV may be calculated as described above in relation to Equations 6 or 7. Note that the feature geometry 1008 may be estimated as described above in connection with FIG. 9.

Figure 10B:
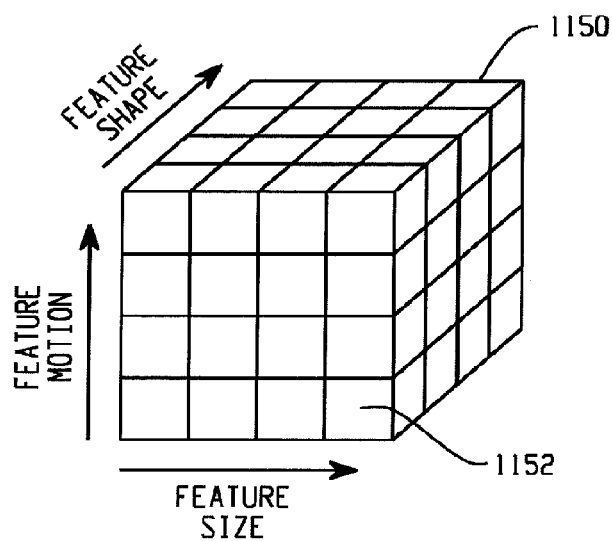
FIG. 10B depicts a data structure.

The motion compensator 1104, which receives the quantitative data from the data generator 1102, operates in cooperation with a compensation function 1106 to generate the motion compensated quantitative data 1010. In one implementation, the motion compensator calculates a suitable motion compensation function S as described above in relation to Equation 10. In another implementation illustrated schematically in FIG. 10B, the compensation function 1106 is obtained from a lookup table or other data structure 1150 that is stored in a suitable computer readable memory. More particularly, the data structure 1150 includes a plurality of motion compensation values 1152 calculated as described above in relation to Equation 10 and FIG. 8. The motion compensation values 1152 are indexed or otherwise accessed according to the feature motion, feature size, feature shape, and/or other relevant variables. Interpolation between various entries 1152 in the data structure may be performed as desired. Note that the feature motion 1006 may be estimated as described above in connection with FIG. 9.

The motion compensator 1104 applies the compensation function 1106 to the quantitative data, for example as described above in connection with Equation 11. The motion compensated quantitative data 1010 may be presented to a clinician or other human user via the user interface 1012, either alone or in combination with other relevant data. Thus, for example, the quantitative data may be presented concurrently with one or more of the activity data 1002, the quantitative data from the quantitative data generator 1102, the feature geometry 1008, a compensation factor, or a representation of the feature shape or motion. As another variation, the user may be afforded an opportunity to enter, confirm and/or revise the lesion size or motion, the compensation value, or other relevant data.

Figure 11:
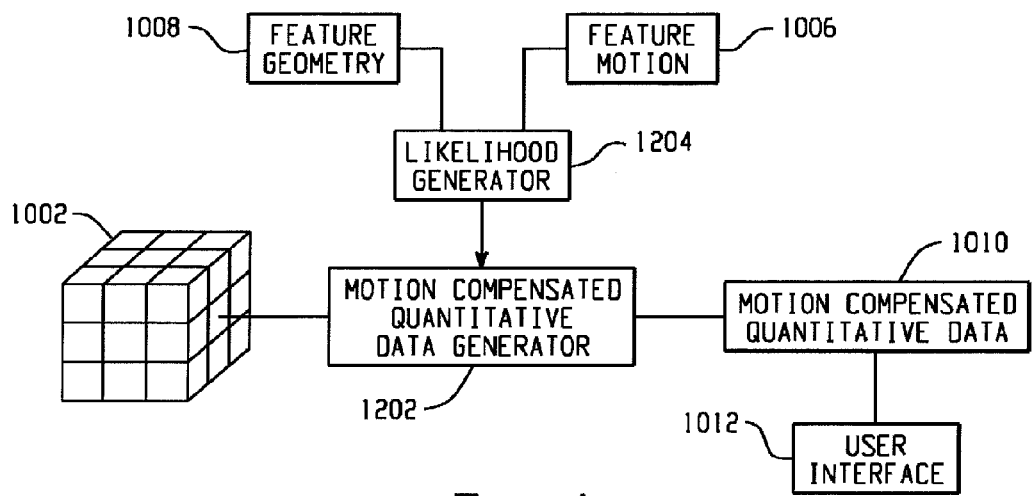
FIG. 11 depicts a motion compensated quantitative data generator.

Another implementation of the motion compensated quantitative data generator will now be described in relation to FIG. 11. As illustrated, a motion compensated quantitative data generator 1202 operates in conjunction with a likelihood generator 1204 to generate the motion compensated quantitative data 1010.

The likelihood generator 1204 uses the feature geometry information 1008 and/or the feature motion information 1006 to determine a probability of or likelihood that the lesion or other feature visited the various locations in the activity data 1002 space during the image acquisition, for example by calculating the probability density $p(x)$ as described above. The motion compensated quantitative data generator 1202 uses the activity data 1002 and the likelihood information to generate the motion compensated quantitative data. The likelihood information thus serves as a motion compensation function that compensates for motion artifacts in the activity data 1002. Where the motion compensated quantitative data 1010 includes a motion compensated mean SUV, the SUV can be calculated as described above in relation to Equation 15. Note that, where the feature includes a plurality of sub-regions, the SUV calculation may be performed for each of the sub-regions, with the results being combined to generate a composite SUV. The motion compensated quantitative data 1010 and/or other relevant information may be presented to the user via the user interface 1012.

Figure 12:
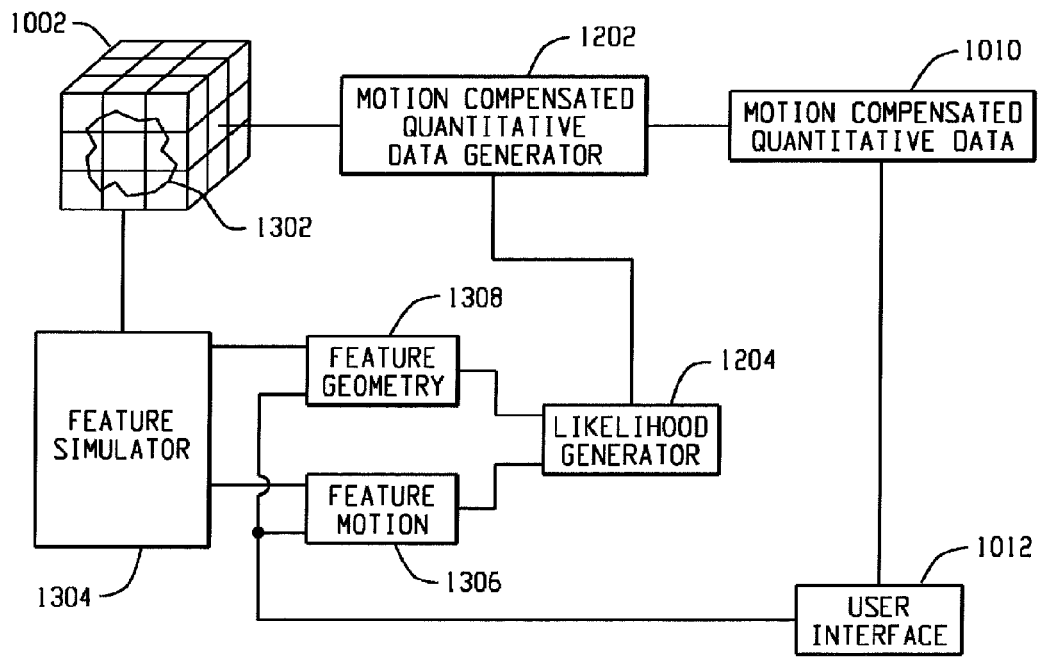
FIG. 12 depicts a motion compensated quantitative data generator.

Another implementation of the motion compensated data generator will now be described in relation to FIG. 12. As illustrated, the system is similar to that described above in relation to FIG. 11. The system also includes a feature simulator 1304 that generates a simulated or virtual feature that approximates a feature 1302 present in the activity data 1002. In one implementation, the feature simulator 1304 identifies feature parameters such as feature activity information, feature geometry information 1308 and/or feature motion information 1306 that produce a virtual feature that approximates the actual feature 1302. Such a simulation may be performed, for example, by iteratively adjusting the activity, geometry 1308 and/or motion 1306 parameters according to a suitable optimization function. In another implementation, the parameters 1306, 1308 are adjusted by a human user via the user interface 1012, with the simulated feature being suitably displayed in relation to the actual feature 1302 for evaluation by the user. Suitable simulation techniques are also described in commonly-owned U.S. Patent Publication No. 2009/0273610 A1 filed May 3, 2005 and published as WO 2006/117706 A1 on Nov. 19, 2006, both entitled Virtual Lesion Quantification, which application and publication are expressly incorporated by reference in their entireties herein. Note that the feature simulator 1304 and its operator interface may be implemented on a different computer than the data generator 1202 and/or the likelihood generator 1204.

Figure 13:
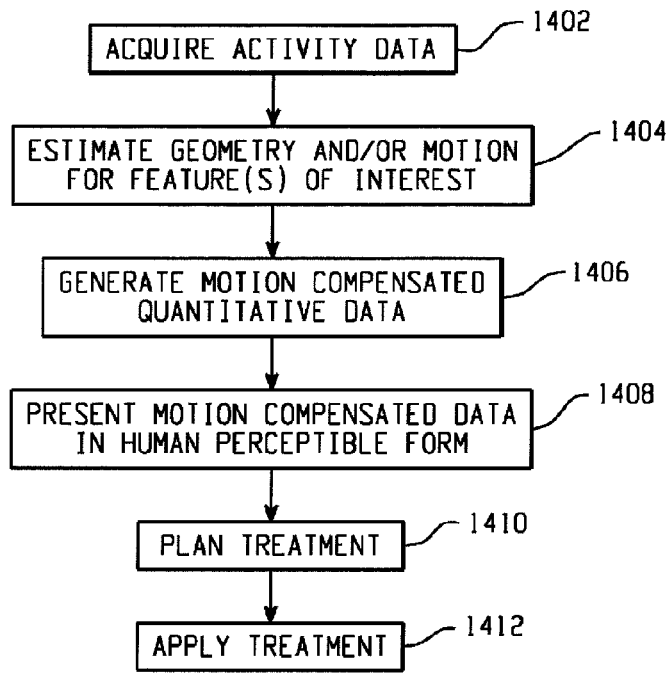
FIG. 13 depicts a method.

Operation will now be described in relation to FIG. 13.

Activity data indicative of a human patient or other object under examination is acquired at 1402, for example by way of a nuclear medical imaging scan. At least a portion of the object may undergo periodic or gross motion during the scan.

At 1404, the geometry and/or motion of one or more features of interest present in the activity data are estimated.

At 1406, the activity, geometry, and/or motion information are used to generate motion compensated quantitative data indicative of the feature(s) of interest. Note that the motion compensated data may be generated at a time and place that is removed from the data acquisition and/or estimation steps.

At 1408, the motion compensated data is presented in a human perceptible form.

At 1410, the motion compensation data is used to plan a suitable treatment for application to the object.

The planned treatment is applied 1412. In one implementation, the treatment includes motion tracking as described above. In other, such tracking is not employed. Note that the treatment may be applied at a time and place that is removed from the treatment planning operation.

Figure 14:
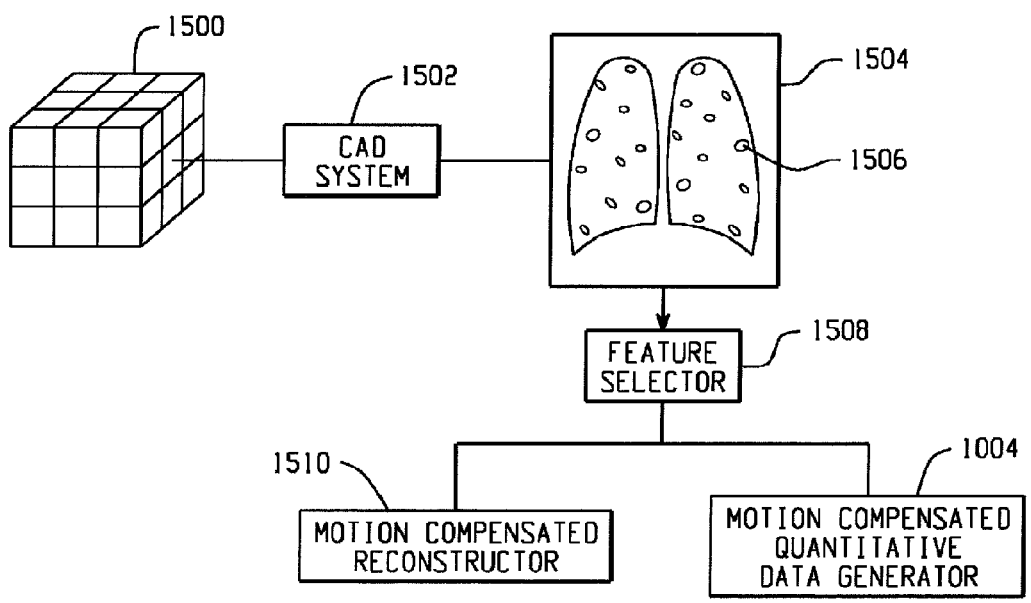
FIG. 14 depicts a feature analysis system.

Another application of the foregoing techniques will now be described in relation to FIG. 14. As illustrated, a system includes a computer aided detection (CAD) system 1502, feature selector 1508, a motion compensated reconstructor 1510, and a motion compensated quantitative data generator 1004.

The CAD system 1502 identifies suspected lesions, pathologies or other features 1506 present in image data 1500 indicative of an object. Note that the image data 1500 may include data generated using more than one imaging modality, for example in the case of a hybrid PET/CT, PET/MR, SPECT/CT, or other system. The image data 1500 may include motion artifacts.

In the illustrated example, the CAD system 1502 is configured as a known lung nodule detection system that identifies suspicious nodules, for example based on acquired CT or x-ray attenuation data. In some cases, the CAD system 1502 may identify a plurality of suspicious features 1506. These features may be identified with varying degrees of confidence or may otherwise be of varying interest to the clinician or other user.

As indicated generally at 1504, the image data 1500 and/or one or more of the identified features 1506 are presented to the user, for example via a computer-implemented GUI. Note that the presented activity data may include motion artifacts due to respiratory or other motion. As the image data 1500 may contain a number of such features 1506, some of which may be of less interest to the clinician, performing a motion compensated reconstruction of all of the features 1506 may not be warranted in terms of computing resources and time, system complexity, or the like.

The feature selector 1508 selects various of the features for analysis. In one implementation, all or a first subset of the features 1506 are selected, and the motion compensated quantitative data generator 1004 generates motion compensated quantitative data that includes a compensation for motion of those features during the data acquisition. A second subset of the features 1506 may also be selected, and the motion compensated reconstructor 1510 performs a reconstruction of that includes a compensation for motion of those features 1506 during the data acquisition. Suitable motion compensated reconstruction techniques are disclosed, for example, in commonly-owned U.S. Provisional Patent Publication No. 2010/0202664 A1 Application Ser. No. 60/951,968 filed Jul. 26, 2007 and entitled Motion Correction in Nuclear Imaging, which application is expressly incorporated by reference in its entirety herein. The quantitative data and motion compensated reconstruction is presented to the in a desired format via the user interface.

Note that various feature selection techniques are contemplated. For example, the features 1506 to be included in the first and second feature subsets may be automatically selected based on an evaluation of the size, activity, or other feature 1506 characteristics, the confidence with which the CAD system 1502 identified a particular feature 1506 as suspect, and/or other selection criteria. Note that the selection criteria are ordinarily established so that features that are more likely to require further or more detailed evaluation (e.g., ambiguous or particularly suspicious features) are included in the second subset. As another example, features 1506 to be included in the first and/or second subsets are identified by the user and selected accordingly. Note also that the CAD system 1502 may be omitted, in which case the features 1506 may be identified by the clinician or other user.

The foregoing motion compensation techniques find particular application to quantification of lesions or other features present in organs that are subject to respiratory and/or cardiac motion. Non-limiting examples of such organs include but are not limited to the liver, lung, and heart. The techniques are also applicable to other organs or regions that are subject non-periodic motion. For example, the prostate may be subject to motion due to the filling of the bladder, the accumulation of intestinal gasses, and the like. It will also be appreciated that the above-described techniques are not limited to SUV calculations and are also applicable to the generation of motion compensated quantitative data indicative of characteristics such as hypoxia, apoptosis, and perfusion.

The techniques are not limited to use in connection with treatment techniques that employ real time motion tracking, and may be employed in connection with chemotherapy, targeted radiotherapy, molecular therapy, internal and/or external radiotherapy, and other treatment modalities in the absence of such tracking.

As will also be appreciated by those of ordinary skill in the art, the various techniques described above may be implemented by way of computer readable instructions stored on suitable computer readable media. When executed by a computer processor, the instructions cause the computer processor to carry out the described techniques.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

Having thus described the preferred embodiments, the invention is now claimed to be:

1. An apparatus comprising:
   a scanner that acquires projection data indicative of an object that includes a treatment target, wherein the projection data is list mode positron annihilation data and the target is subject to motion during a treatment session;
   a motion modeler that uses projection data acquired during the treatment session to model the motion of the target;
   a treatment device that treats the target during the treatment session, wherein the treatment device varies a spatial location of an applied treatment as a function of the model of the motion.

2. The apparatus of claim 1 wherein the motion modeler models the motion of the target and the treatment device varies the spatial location of the treatment in substantially real time, whereby the spatial location of the applied treatment tracks the spatial location of the target.

3. The apparatus of claim 1 wherein the motion modeler models the motion of a center of activity a plurality of times during the treatment session.

4. The apparatus of claim 1 including:
   a filter that filters the projection data to identify projection data indicative of a region of interest of the object;
   a characteristic processor that processes the filtered projection data to identify a characteristic feature of the region of interest, wherein the filter and characteristic processor operate to identify the characteristic feature at each of a plurality of times during the treatment session.

5. A computer readable memory containing instructions which, when executed by a processor, cause the processor to carry out a method that includes:
   selecting projection data indicative of radio nuclide decays occurring in a region of interest of an object during a treatment session in which a treatment is applied to a moving target of the object;
   using the selected projection data to identify a characteristic feature of the region of interest;
   modeling the motion of the characteristic feature;
   repeating the steps of selecting projection data, using the selected projection data, and modeling a plurality of times during the treatment session.

6. The computer readable memory of claim 5 wherein the method includes storing the motion model in a computer readable memory accessible to a treatment device that applies the treatment.

7. The computer readable memory of claim 5 wherein selecting projection data includes disregarding projection data that does not intersect the region of interest.

8. The computer readable memory of claim 5 wherein using the selected projection data includes backprojecting the selected projection data and using the backprojected data to identify the characteristic feature.

9. The computer readable memory of claim 5 wherein the projection data includes lines of response indicative of positron annihilations and using the selected projection data includes determining a distance between a first line of response and a second line of response.

10. The computer readable memory of claim 5 wherein modeling the motion of the characteristic feature includes determining a spatial position of the characteristic feature.

11. The computer readable memory of claim 5 wherein modeling a motion of the characteristic feature includes using a motion model generated during the treatment to predict an expected motion of the characteristic feature.

12. The computer readable memory of claim 5 wherein repeating includes repeating the steps of selecting projection data, using the selected projection data, and modeling a plurality of times in substantially real time so as to track the motion of the characteristic feature.

13. A method comprising:
   selecting, during a treatment session in which a treatment is applied to a target of the an object, raw data acquired during the treatment session that is indicative of radionuclide decays in a region of interest of -the object, wherein the motion of the region of interest is representative of the motion of the target;
   using the selected raw data to model a motion of the target with a processor;
   adjusting, as a function of the motion model, a characteristic of the applied treatment with the processor;
   repeating the steps of selecting, using, and adjusting during the treatment session.

14. The method of claim 13 wherein the region of interest includes the target.

15. The method of claim 13 wherein the treatment includes the a localized application of energy to the target and adjusting includes adjusting a spatial location at which the energy is applied.

16. A method comprising:
   presenting first image data indicative of an object to a human user, wherein the first image data includes a plurality of features;
   selecting a first feature;
   generating quantitative data indicative of the first feature, wherein the quantitative data includes a motion compensated uptake value;
   selecting a second feature;
   performing, via a processor, a motion compensated reconstruction that compensates for a motion of the second feature.

17. The method of claim 16 wherein selecting the second feature includes selecting a
   feature identified by the human user.

18. The method of claim 16 wherein the method includes evaluating a characteristic
   of a feature and selecting the second feature includes selecting the second feature based on a result of the evaluation.

19. The method of claim 16 including using a computer aided detection system to identify the first and second features.

* * * * *